United States Patent [19]
Sitte et al.

[11] Patent Number: 4,511,224
[45] Date of Patent: Apr. 16, 1985

[54] MICROTOME WITH SPECIMEN ILLUMINATION SYSTEM

[75] Inventors: Helmuth Sitte, Seefeld/Tirol, Austria; Terry W. Cooper, Milton Keynes, Great Britain; Heinrich Kleber, Vienna, Austria

[73] Assignee: C. Reichert Optische Werke, AG, Vienna, Austria

[21] Appl. No.: 519,283

[22] Filed: Aug. 1, 1983

[30] Foreign Application Priority Data

Jun. 30, 1982 [DE] Fed. Rep. of Germany ...... 3224449
Sep. 29, 1982 [DE] Fed. Rep. of Germany ...... 3235951

[51] Int. Cl.³ .......................... G02B 21/06; B23Q 3/00
[52] U.S. Cl. .................... 350/523; 83/915.5; 269/11
[58] Field of Search ................. 350/523, 527; 83/451, 83/520–521, 915.5; 356/30–31; 51/165.72, 216 LP; 125/35; 408/16; 269/11; 65/4.3, 10.2

[56] References Cited

U.S. PATENT DOCUMENTS

| 2,440,950 | 5/1948 | Hill | 83/520 |
| 3,103,844 | 9/1963 | Persson | 83/915.5 |
| 3,989,379 | 11/1976 | Eickhorst | 356/30 |
| 4,251,128 | 2/1981 | Feinbloom | 350/523 |

FOREIGN PATENT DOCUMENTS

125954 9/1980 Japan ..................... 408/16

Primary Examiner—William H. Punter
Attorney, Agent, or Firm—A. H. Spencer; S. Raines

[57] ABSTRACT

A microtome, in particular an ultramicrotome, having a specimen carrier which can be moved relative to a knife. The specimen carrier includes a clamping aperture for holding a specimen. A light source is located inside the clamping aperture in the specimen carrier so that light is transmitted, from the rear of the clamping aperture, through a specimen block which is composed of a transparent material and through the specimen.

10 Claims, 3 Drawing Figures

MICROTOME WITH SPECIMEN ILLUMINATION SYSTEM

BACKGROUND OF THE INVENTION

This invention relates to microtomes, more particularly ultramicrotomes, of the type having a specimen carrier which can be moved relative to a knife, the specimen carrier possessing a clamping aperture for the purpose of holding a specimen, and a light source for illuminating the specimen.

The majority of specimens cannot be sliced in their natural form and condition. In most cases, the preparation of such specimens (small pieces of animal or human organs, such as liver, spleen or brain, residues centrifuged from body fluids, parts of plants or microorganisms, or tissue-cultures, etc.) is required. This usually involves a stabilization treatment by means of an aldehyde and/or a heavy metal, followed by dewatering and embedding the specimen in a plastic material which is normally transparent or translucent (e.g. an epoxide or a polyester).

The cylindrical, flat or prismatic, "specimen blocks" which are obtained by means of this process, and which can readily be cut, are clamped in a specimen carrier and, after trimming to size, the specimen blocks are sliced into the thin sections for examination under a microscope or an electron microscope. The slicing operation is usually carried out with a knife made of metal, glass or diamond.

The ability to observe the specimen/knife region in an extremely precise manner is a prerequisite for the production of perfect thin sections in a microtome and especially in an ultramicrotome. In particular, the success of a slicing operation of this type depends critically on selecting the correct region of the specimen block. For this purpose, especially in the case of ultramicrotomes, a stereomicroscope and a light source are provided, the former for observing the specimen/knife region and the latter for illuminating it. The light source is installed above the specimen/knife region, and/or beneath it, and is frequently adjustable in order to enable it to be aligned as precisely as possible with the cutting edge of the knife, and/or the surface of the specimen block to be cut.

Up to the present time, the means for enabling the specimen/knife region to be observed in a precise manner has not been completely satisfactory. Thus, it is not always possible for an operator to select the correct region of the specimen block because the internal structure of the specimens, the fine surface structure, or very small objects, are poorly displayed and cannot be identified so reliably that the details of interest occur in the selected slice. Sometimes interesting regions of the specimen are unintentionally removed during the trimming operation, and have hence been lost, so that the surface of the prepared section contains regions which not only are of no interest, but which may interfere with the cutting process (e.g. hard inclusions, collagen fibers which are difficult to cut, or fat cells). Neither incident-light illumination by means of cold-light tubes or similar light sources above the specimen, as generally employed, nor dark-field illumination, which is often employed to illuminate the specimen/knife region from below (sublevel illumination), is satisfactory to facilitate identifying the desired areas of the specimen. The only effective procedure involves trimming the specimen while it is fastened to the specimen carrier, during which process it is observed from the front by means of a mirror system ("structure viewer").

Furthermore, when an adjustment of the light source (indicent-light illumination, and/or sublevel illumination), or a setting of the specimen in relation to a light source, has been found to give optimum illumination of the specimen, it is exceedingly irritating if the position of the specimen, relative to the knife, has to be altered in order to obtain thin sections of optimum quality. This is because the illumination must be readjusted in order to ensure that the desired precision of observation is maintained. This situation arises, for example, in the case of specimen carriers which are combined, for the purpose of angular adjustment, with so-called segment arcs, along which they can be swung horizontally about a pivot axis which lies approximately on the cutting edge of the knife.

OBJECTS OF THE INVENTION

An object of the present invention is to avoid the above-mentioned disadvantages, to provide a microtome, in particular an ultramicrotome, having an improved illuminating system which brings out the fine structures in a specimen more effectively than hitherto, and at the same time eliminates the need for readjustments whenever the position of the specimen is altered.

A further object is to permit the successful and easy use of a "structure viewer" in all possible positions of the specimen block to select interesting regions of the specimen for cutting, and/or to eliminate those regions of the specimen which are not of interest, in a systematic manner.

BRIEF DESCRIPTION OF THE INVENTION

According to the present invention, we provide a microtome having a specimen carrier which can be moved relative to a knife, the specimen carrier being provided with a clamping aperture for holding a specimen, and a light source for illuminating the specimen, the light source being located inside the clamping aperture in the specimen carrier.

A miniature filament-type light bulb, for example, may be located inside the clamping aperture of the specimen carrier as the light source, this bulb being installed in a manner such that the light from it passes through the specimen block when the latter is in its clamped state.

A surprising discovery with this arrangement is that the internal structure of the specimen is clearly displayed as a result of the transparency or translucency of the material which is used for embedding the specimen. The light source may be installed in the bottom of the clamping aperture, or at its rear end, for example, in a segment arc, in a manner such that, when the specimen block is in the clamped state, it is located behind this block so that the light passes through the block in the longitudinal direction of the clamping aperture. However, it is also possible to illuminate the specimen block from the inside, if the light source is installed beside it, in the wall of the clamping aperture, and radiates into the specimen block at a defined angle. In a further embodiment of the invention, a deflecting mirror can be installed in the clamping aperture as the light source, this mirror directing the light from a lamp outside the clamping aperture into the specimen block. This arrangement prevents the specimen from being heated above a permissible temperature, a factor which must be taken into account especially when working in the cryorange. In yet a further embodiment, heating of the specimen is avoided by guiding the light into the specimen block via a fiber-type light guide, or similar device, the end of the light guide which emits the light being located in the clamping aperture, or in the wall of this aperture, in a manner such that concentrated light is directed into the specimen block. In some circumstances, a filter, serving as a heat barrier, may be installed between the light source (filament-type bulb, deflecting mirror, end of the fiber-type light guide) which is present in the clamping aperture, and the specimen block.

Within the scope of the invention, it is possible for the internal illumination of the specimen block to be switched on and off independently of any other illumination sources which may be present, this being effected by a suitable switch. In addition, certain advantageous combinations involving the incident-light light source, and/or the sublevel light source, and the internal illumination, according to the invention, can be rendered settable by means of a handle and a combination switch to facilitate advantageous varieties of mixed illumination to be obtained, without having to operate a plurality of switches separately.

Since the light source is installed in the specimen carrier, it moves with the specimen carrier and, thus, follows any adjusting movements of the specimen carrier for the purpose of adjusting the specimen in relation to the knife. In consequence of this, the quality of the illumination remains unchanged at all times, even during pivoting adjustments of the specimen carrier, for example, on a segment arc, no matter how extensive these movements may be.

BRIEF DESCRIPTION OF THE DRAWINGS

Illustrative embodiments of the invention are described below with reference to the drawings in which.

DETAILED DESCRIPTION OF THE INVENTION

Figure 1:
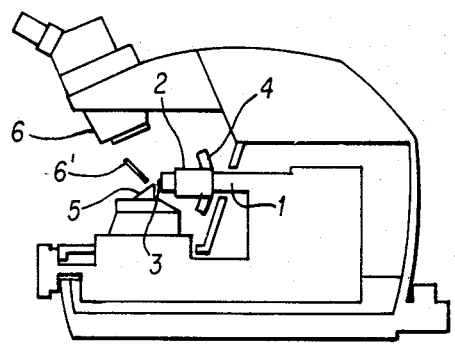
FIG. 1 is a diagrammatic side view of an ultramicrotome partially in section.

In FIG. 1 an ultramicrotome is illustrated having a specimen arm 1 which can move upwards and downwards. A specimen carrier 2, for a specimen or prepration 3, is located at the front end of the specimen arm 1, the specimen 3 being attached to the specimen carrier 2, which is fastened to a segment arc 4 in a manner which permits it to swing horizontally in such a way that the angular position of the preparation 3, relative to the cutting edge of a knife 5, can be altered. The segment arc 4 enables the specimen carrier 2 to be angularly adjusted about a pivot point which lies virtually on the cutting edge of the knife.

To permit observation, a stereomicroscope 6 is provided above the region occupied by the specimen 3 and the knife 5. A deflecting mirror 6', a so-called "structure viewer" is arranged in the light path of the stereomicroscope 6; this "viewer" enables the end face of the specimen 3 to be observed and examined for the purpose of trimming it in a precise manner. The ultramicrotome shown in FIG. 1 is of known design and for this reason details of its construction are not described.

Figure 2:
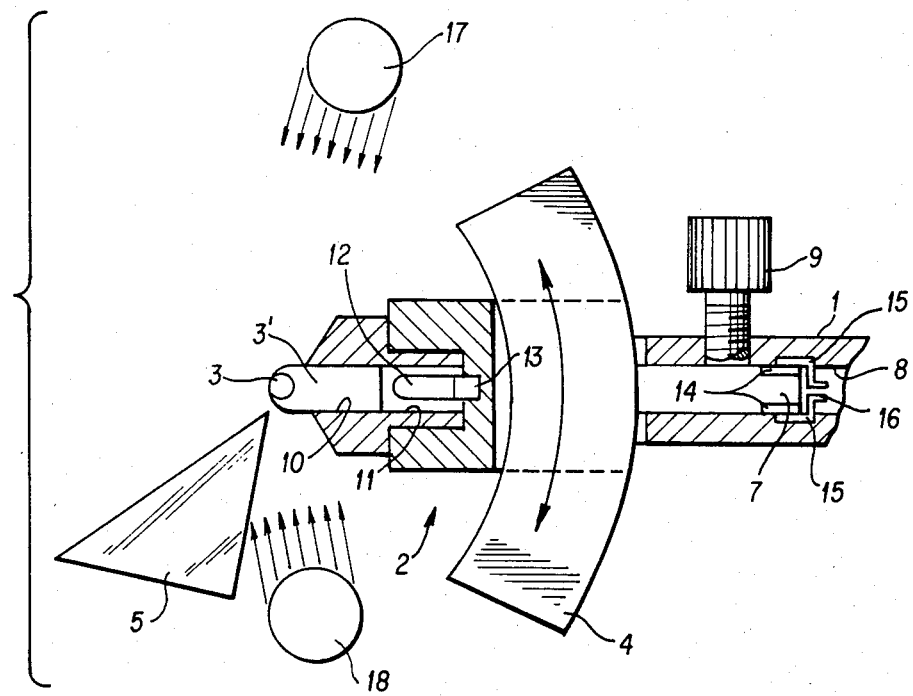
FIG. 2 is a detailed representation of a specimen carrier, according to the invention, in longitudinal section, this specimen carrier being intended for use in the ultramicrotome shown in FIG. 1.

In FIG. 2, the specimen carrier 2 is clamped to the segment arc 4, and can be angularly adjusted in the directions shown by the double arrows in the drawing.

A journal-shaped projection 7 is located on the rear surface of the segment arc 4, or on the rear surface of the specimen carrier 2. The projection 7 can be pushed into a bore 8 in the specimen arm 1 in which it can be securely clamped by means of a locking screw 9.

At its front end, the specimen carrier 2 possesses a clamping aperture 10 for the specimen 3 which is cast into a specimen block 3' which is composed of a transparent material, such as paraffin or a plastic material. The clamping aperture 10 is deep enough to leave a space 11 when the specimen block 3' is clamped within the clamping aperture. The space 11 extends from one end of the specimen block 3' to the bottom of the clamping aperture 10. In the space 11 a light source 12 is installed, and comprises a miniature filament-type light bulb. The light source 12 is seated in a holder 13 which is provided at the bottom of the clamping aperture 10. Power supply leads (not shown) to supply power to the holder 13 run outside or inside the segment arc 4 to contact ends 14 at the end of the journal-shaped projection 7. The contact ends 14 form electrically-conducting connections with corresponding contacts 15 in the bore 8 of the specimen arm 1. From the contacts 15, leads 16 run to a source of electrical power (not shown).

An additional light source 17 can be arranged above the specimen carrier 2, and a sublevel light source 18 can be arranged beneath it. Optimum illumination of the specimen 3, or of the specimen/knife region of the ultramicrotome, is provided by these light sources, in conjunction with the direct illumination of the preparation provided by the light source 12.

Figure 3:
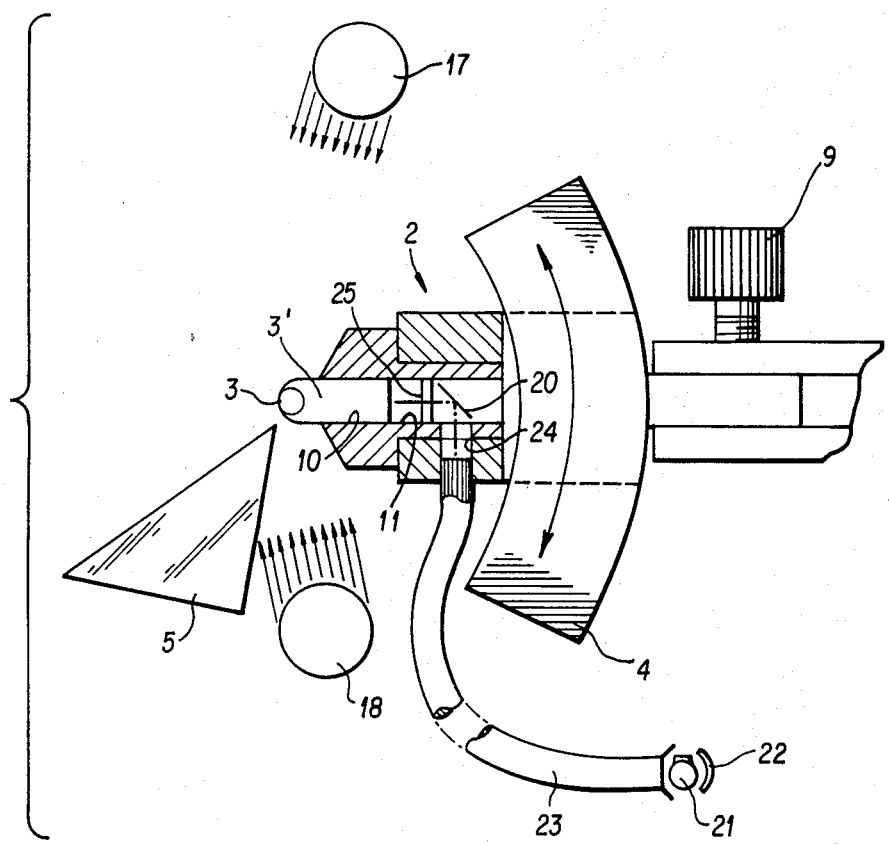
FIG. 3 is a modified embodiment of the specimen carrier shown in FIG. 2.

In FIG. 3, the specimen carrier 2 includes many components which are substantially identical to components shown in FIG. 2, and like components are marked with like reference numbers. However, in the embodiment shown in FIG. 3, a deflecting mirror 20 is located in the space 11 within the clamping aperture 10, instead of the light bulb 12 used in the embodiment shown in FIG. 2. A filament-type light bulb 21, having a reflector 22, supplies light to the deflecting mirror 20 along a fiber-type light guide 23, the end of which is secured in a lateral hole 24 in the specimen carrier 2. The deflecting mirror 20 deflects the light from the light bulb 21 through 90° and radiates it into the specimen block 3'. A heat-absorbing screen 25, such as a thin crystal-glass plate, is installed between the deflecting mirror 20 and the specimen block 3'. The screen 25 protects the specimen block 3' from heating which occurs as a result of thermal radiation. (Clearly a heat-absorbing screen, or a heat filter, can be similarly provided in the embodiment of the invention shown in FIG. 2, if the specimen block 3' needs to be protected from thermal radiation; this is particularly important when working at low temperatures).

Since the fiber-type light guide 23 conducts light with comparatively low losses, the filament-type light bulb 21 can be located on the ultramicrotome, and the length of the fiber-type light guide 23 can be made sufficiently long to prevent it from impeding either the movement of the specimen arm 1, or the adjustment of the specimen carrier 2 on the segment arc 4.

It is possible, within the scope of the invention, to devise modifications to the illustrative embodiments described above. For example, the miniature filament-type light bulb 12, or the deflecting mirror 20, can be located in an extension of the clamping aperture 10, and hence of the space 11, or in the segment arc 4, behind the bottom of the clamping aperture. However, the light radiated by the light source must enter the specimen block 3' in such a manner that the internal structure of the specimen 3 is rendered bright, and is thereby displayed, due to the transparency or translucency of the specimen block 3'.

We claim:

1. A microtome having a specimen carrier which can be moved relative to a knife, the specimen carrier being provided with a clamping aperture for holding a specimen, and a light source for illuminating the specimen, the light source being located inside the clamping aperture in the specimen carrier.

2. A microtome according to claim 1 in which the light source is located at the bottom of the clamping aperture behind the specimen.

3. A microtome according to claim 1 in which at least one additional light source is provided to illuminate the specimen/knife region of the microtome from above.

4. A microtome according to claim 1 in which the light source is a miniature filament-type light bulb.

5. A microtome according to claim 1 in which the light source comprises a deflecting mirror to which light can be directed from a source of illumination located outside the specimen carrier.

6. A microtome according to claim 5 in which the end of a fiber-type light guide is secured in a lateral bore in the specimen carrier, which bore is open towards the clamping aperture, the light guide serving to direct light from said source of illumination to said mirror.

7. A microtome according to claim 1 in which a heat-absorbing screen is installed between the specimen and the light source, the screen being transparent to light.

8. A microtome according to claim 1 in which the specimen carrier is angularly adjustable about a pivot point which lies virtually on the cutting edge of the knife so that the angular adjustment is along an arc of a circle.

9. A microtome according to claim 3 in which the light source is provided with switching means whereby it can be switched independently of said at least one additional light source.

10. A microtome according to claim 3 in which the light source is provided with switching means whereby it can be switched in combination with at least one additional light source.

* * * * *